United States Patent [19]

John

[11] Patent Number: 4,913,160
[45] Date of Patent: Apr. 3, 1990

[54] ELECTROENCEPHALOGRAPHIC SYSTEM AND METHOD USING FACTOR STRUCTURE OF THE EVOKED POTENTIALS

[75] Inventor: Erwin R. John, Mamaroneck, N.Y.

[73] Assignee: New York University, New York, N.Y.

[21] Appl. No.: 171,109

[22] Filed: Mar. 21, 1988

Related U.S. Application Data

[63] Continuation-in-part of Ser. No. 103,181, Sep. 30, 1987, abandoned.

[51] Int. Cl.[4] .............................................. A61B 5/04
[52] U.S. Cl. ..................................... 128/731; 128/745; 128/746
[58] Field of Search ............................. 128/731–732, 128/733, 745–746

[56] References Cited

U.S. PATENT DOCUMENTS

| | | | |
|---|---|---|---|
| 3,780,724 | 12/1973 | John ........................................ | 128/731 |
| 3,799,146 | 3/1974 | John et al. .............................. | 128/731 |
| 3,901,215 | 8/1975 | John ........................................ | 128/731 |
| 4,188,956 | 2/1980 | John ........................................ | 128/731 |
| 4,201,224 | 5/1980 | John ........................................ | 128/731 |
| 4,279,258 | 7/1981 | John ........................................ | 128/731 |
| 4,417,592 | 11/1983 | John ........................................ | 128/731 |
| 4,493,327 | 1/1985 | Bergelson et al. .................... | 128/731 |
| 4,545,388 | 10/1985 | John ........................................ | 128/731 |
| 4,557,270 | 12/1985 | John ........................................ | 128/731 |
| 4,610,259 | 9/1986 | Cohen et al. .......................... | 128/731 |
| 4,705,049 | 11/1987 | John ........................................ | 128/731 |

Primary Examiner—Angela D. Sykes
Attorney, Agent, or Firm—Eliot S. Gerber

[57] ABSTRACT

In an electroencephalographic method and system for the quantitative analysis of brain waves, a programmed sequence of stimuli is automatically presented to a subject to evoke averaged evoked responses (AER's). The AER's are automatically analyzed by factor analysis in which each waveshape is reconstituted, as closely as possible, by a set of "basis waveshapes" (factors) held in memory. The "factor scores" (contributions of each factor) are $Z$ transformed as a comparison against results from a normal population, and displayed as color-coded topographic maps of the head.

14 Claims, 2 Drawing Sheets

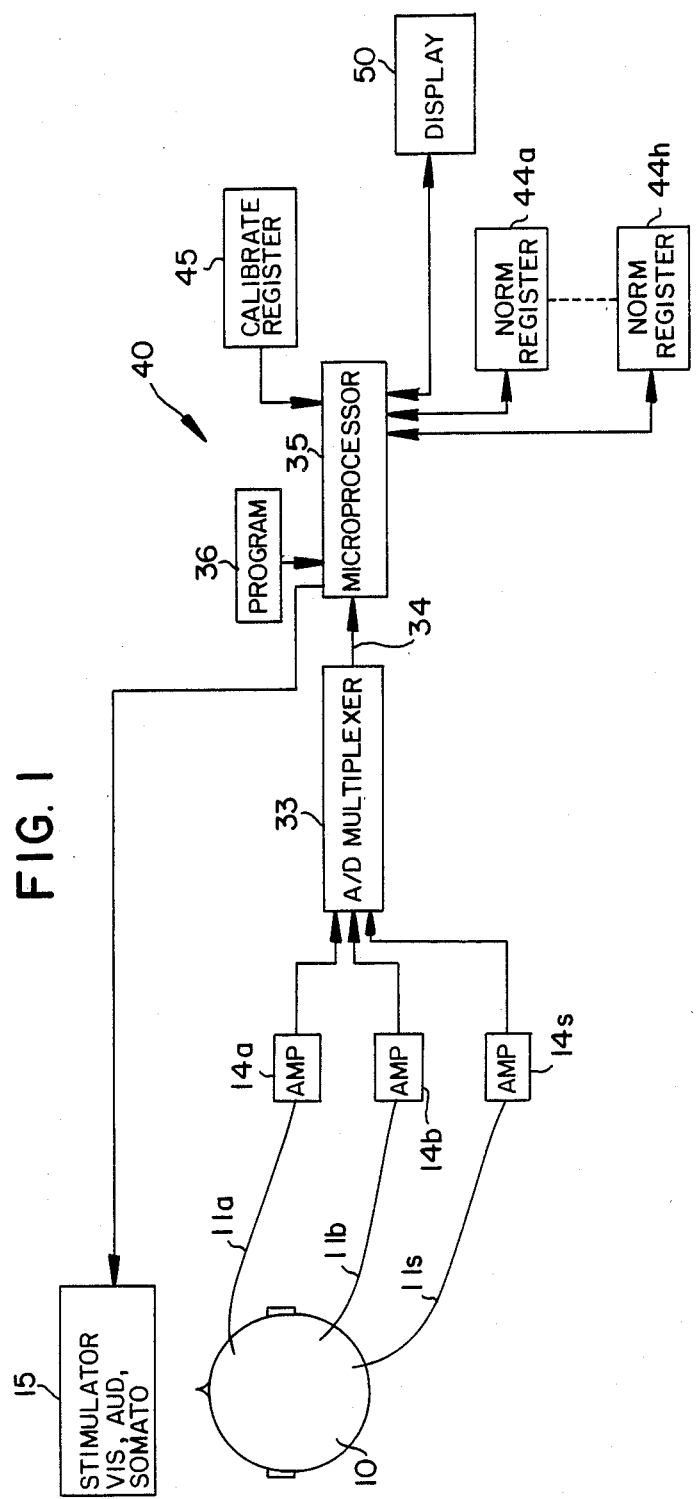

ELECTROENCEPHALOGRAPHIC SYSTEM AND METHOD USING FACTOR STRUCTURE OF THE EVOKED POTENTIALS

This application is a continuation-in-part application based upon a copending Application Ser. No. 07/103,181, filed Sept. 30, 1987 and entitled "Electrophysiological System and Analysis Method Using Factor Structure of the Evoked Potentials" (now abandoned).

BACKGROUND OF THE INVENTION

The present invention relates to medical systems and methods and more particularly to the analysis of human brain waves by quantitative electroencephalography ("QEEG").

Human brain electrical activity ("brainwaves") may be detected by electrodes placed on the scalp of a subject. The subject's brainwaves reflect brain functions including information processing and cognition. Individuals suffering from disorders of these functions might benefit from intervention, such as specific pharmaceutical treatment, if precise diagnostic information were available.

A methodology based on digital data processing using computers has been developed, called "neurometrics". It provides quantitative information about brain activity related to anatomical integrity, developmental maturation, and mediation of sensory, perceptual and cognitive processes.

Digital computer-based methods permit examination of those brainwaves which are transient electrical oscillations or "evoked potentials" (EP's) elicited by sensory stimuli, such as visual flashes or auditory clicks. Analyses of EP's provide information about the structural integrity of the brain and yield insights into many aspects of brain function concerned with the reception, encoding, processing, and evaluation of information.

It has been especially difficult to obtain accurate diagnoses of various psychiatric disorders or to confirm the accuracy of such diagnoses by independent measures. Psychiatric diagnosis remains almost entirely dependent upon the subjective interpretation of the patient's verbal behavior during a diagnostic interview. Often, the patient is unable or unwilling to provide meaningful answers to questions about his symptoms or circumstances. The verbal products of a patient, even when provided, are often ambiguous in meaning. Furthermore, it is possible that sufficient information for accurate diagnosis is actually not available by verbal interactions under even the most favorable conditions. Verbal statements may be considered as being symptoms, and similar symptoms can be produced by various underlying causes. Objective methods which can directly reveal pathophysiological processes are needed to improve and confirm the accuracy of psychiatric diagnosis.

A series of prior patents and patent applications, naming the inventor of the present application as their inventor, provides a considerable amount of background information regarding details of certain portions of the system and method of the present invention; and consequently these patents and applications are specifically referred to below and incorporated herein by reference.

The patents and applications are as follows:

PATENTS

| Patent No. | Title | Issue Date |
|---|---|---|
| 3,901,215 | Method of Testing the Senses and Cognition of Subjects | August 26, 1975 |
| 4,188,956 | Analysis, Display and Classification of Multivariate Indices of Brain Function -- A Functional Electro-Physiological Brain Scan | February 19, 1980 |
| 4,201,224 | Electroencephalographic Method and System for Quantitative Description of Patient Brain States | May 6, 1980 |
| 4,417,592 | Digital Electroencephalographic Instrument and Method | November 29, 1983 |
| 4,545,388 | Self-Normed Brain State Monitoring | October 8, 1985 |
| 4,557,270 | Electroencephalographic System For Intra-Operative Open-Heart Surgery | December 10, 1985 |
| 4,705,049 | Intraoperative Monitoring . . . Self-Optimizing Digital Comb Filter | November 10, 1987 |

APPLICATIONS

| Application No. | Title | Filing Date |
|---|---|---|
| 044,438 | Electroencephalographic System Data Display | August 4, 1986 |

OBJECTIVES AND FEATURES OF THE INVENTION

It is an objective of the present invention to provide an improved system and method in quantitative electroencephalography (QEEG) in which, using averaged evoked potentials (AEP), patients may objectively be diagnosed on the basis of a statistical analysis of their brainwaves, with an improved degree of accuracy as being normal or abnormal; and, if diagnosed as abnormal, may be further diagnosed, for example, as unipolar depressive, bipolar depressive, schizophrenic, demented or alcoholic.

It is a further objective of the present invention that the testing of the subject may be performed in a non-invasive manner using painless and removable scalp electrodes.

It is a further objective of the present invention that such testing include stimulus which is automatically presented to the patient, under computer control, so that the testing may be performed by technical personnel, who need not be physicians.

It is a still further objective of the present invention to provide such a system and method which analyzes the brainwave data automatically in a digital computer-based system and which presents the results of the statistical analysis in the form of a readily comprehended head-like topographic map, which is color-coded to show the degree of abnormality.

It is a feature of the present invention to provide a method and system of analyzing the brain waves of a human subject to determine the presence, degree and type of potential abnormality. For example, the method and system may be used to diagnose psychiatric disorders such as unipolar and bipolar depressions. The method consists of the steps, in sequence, of first securing a plurality of removable electrodes to the scalp of the patient and, secondly, automatically presenting a sequence of stimuli, for example flashes, to produce visual evoked potentials and clicks to produce auditory evoked potentials. The stimuli are presented to the patient to evoke brainwave potentials (EP) at the electrodes.

The method also includes the steps of detecting the EP brainwaves amplifying the detected brainwaves using a low-noise high-gain amplification, converting the amplified brainwaves into digital form using an A/D converter and, in a digital data processing computer system, averaging the digitalized brainwaves to produce average evoked potentials (AEP) for analysis.

The computer system then analyzes the average evoked potentials (AEP) by factor analysis, in which each AEP waveshape from each electrode is compared to pre-formulated waveform factors stored in computer memory to determine the weighting that each pre-formulated waveform factor contributes to each AEP, to thereby produce a factor score. The computer system then subjects this factor score to Z-transformation, wherein each of the factor scores is compared to norms stored in computer memory to produce a determination of normalcy or the degree of abnormality of each EP waveshape.

The normalcy and degree of abnormality is displayed on a color-coded topographic map. The map is a head diagram on which each area of the head represents an electrode location. The color represents normalcy or the degree of abnormality.

BRIEF DESCRIPTION OF THE DRAWINGS

Other objectives and features of the present invention will be apparent from the following detailed description taken in conjunction with the accompanying drawings.

In the drawings:

FIG. 1 is a block schematic drawing of the apparatus of the present invention;

FIG. 4 is an enlarged view of one of the blocks of the map of FIG. 3.

DETAILED DESCRIPTION OF THE INVENTION

Figure 3:
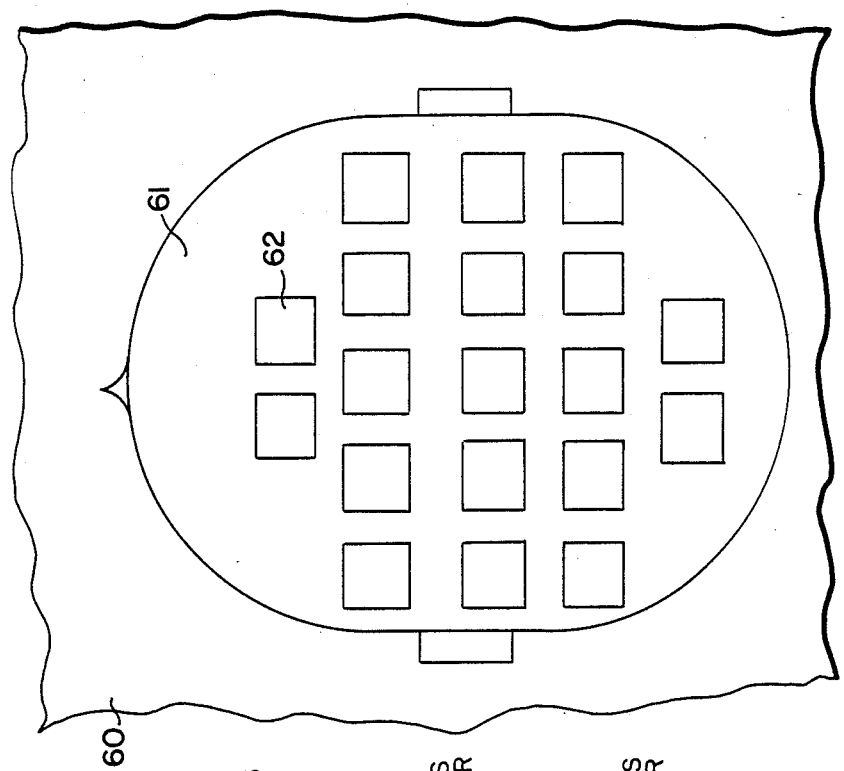
FIG. 3 is a topographic map of the head, as seen from above, displayed on a CRT monitor.

In the setting, for example, of a doctor's office or a hospital, the patient to be examined is seated and a set of electrodes is connected to his scalp using conductive paste on the electrodes. Preferaby the electrodes are in a stretch-band and comprise the electrode set of the International 10/20 Electrode Placement System.

As shown in FIG. 1, the head 10 of the patient is connected to the set of electrodes. Only three pairs of electrodes 11a, 11b and 11s are shown in FIG. 1 to simplify the drawing. However, preferably the 19 electrodes of the International 10/20 Electrode Placement System are used to provide 19 monopolar or 8 bipolar (constructed or direct) derivations. The preferred bipolar derivations would be $F_7 T_3$, $F_8 T_4$, $T_3 T_5$, $T_4 T_6$, $C_3$, $C_{\bar{z}}$, $C_4 C_{\underline{z}}$, $P_3 O_1$ and $P_4 O_2$. However, other bipolar derivations might be constructed. Further information regarding the computed construction of pair derivations may be obtained from the inventor's prior patent entitled "System and Method For Electrode Pair Derivations in Electroencephalography", Pat. No. 4,411,273, incorporated by reference herein.

In FIG. 1, each of the electrode leads 11a–11n, preferably nineteen such leads, is connected to its own individual amplifier. As illustrated, the electrode 11a is connected to the amplifier 14a, the electrode 11b is connected to the amplifier 14b and the electrode 11s is connected to the amplifier 14s.

Each of the amplifiers 14a–14s has an input isolation switch to protect against current leakage; for example, a suitable isolation switch is a photo-diode - light-emitting diode (LED) isolation coupler. In addition, each amplifier input is protected from electrical interference by use of a radio-frequency filter and a 60-cycle notch filter. Preferably each amplifier has a frequency range of 0.5 to 100 Hz, gain of 10,000, a common mode rejection of 160 DB, and noise of less than 2 microvolts. Such high-gain low-noise amplifiers are presently commercially available. Each of the 19 inputs is compared (referenced) against an inactive electrode such as an electrode connected to the earlobe.

An analog-to-digital multiplexer (A/D multiplexer) 33 provides a digital output from the nineteen analog amplifiers. The A/D multiplexer 33 samples the EEG waves (outputs of amplifiers 14a–14s) at a rate compatible with their bandwidths, preferably at the rate of 200 to 300 times per second to comply with their 0.05 to 100 Hz bandwidth.

The information from the multiplexer 33 is provided over line 34 to a microprocessor 35. The microprocessor has been programmed by an external software program means, such as a floppy disk recorder, or other input system 36. The microprocessor may be the INTEL 8086, NEC-PD8086 or the LSI 11-23 or other comparable devices.

The program and its controlled microprocessor condition the input signals and insure that they are valid biological signals. Such validity checks on the input signals include calibration measurement, impedance measurements and automatic artifact rejection algorithms. The validity checks are explained in detail in the U.S. Pat. 4,557,270, referred to above and incorporated by reference herein.

The computer system 40 automatically provides a timed set of stimuli from stimulator 15 which may be an audio sound from a speaker, a visual signal from a light flash, or a tactile signal from an electric shock or a vibrator. The patient's brain wave will respond to that stimulus providing an "Evoked Potential" (EP). Those brain waves are averaged to reduce noise, providing an "Average Evoked Response" (AER).

The AER is the sum of samples time locked to the onset of the stimuli divided by the number of samples, to provide an updated average. Preferably the AER is obtained in computer 40, although a special-purpose average response computer of the type disclosed in Clynes U.S. Pat. 3,087,487 or John U.S. Pat. 3,705,297 may be used (both patents being incorporated by reference herein).

The analysis of such averaged evoked response (AER) has generally been by subjective visual examination by neurologists and other similarly highly trained and skilled personnel. Such an examination depends upon the skill and attention of the examiner. A number of methods of computer-assisted analysis of AER's have been suggested in the literature and in prior patents. One such method is that of "factor analysis", which is generally described in E. Roy John, *Neurometrics*, Science, Vol. 196, No. 4297, June 24, 1977, and *Functional Neuroscience*, Vol. II, Neurometrics, pages 59–61 (Erlbaum 1977), both the article and book being incorporated by reference.

"Factor analysis" may be considered a type of "pattern recognition" in which a waveform is reconstructed as closely as possible, by a set of "basis waveshapes" or factors held in memory. There has been considerable research activity, for example, in connection with speech analysis, in connection with pattern recognition methods, for example, using template matching programs. Factor analysis, of AER waveshapes, like other pattern recognition systems, is based on the premise that the waveforms produced by normal persons are similar. The AER waveshapes from normal persons, on the basis of experimental results, have been shown to be sufficiently similar that they may be reconstructed using a small number of factor waveshapes. This makes intuitive sense; one would expect that the brains of different normal people would react to a series of stimuli (flashes, clicks, etc.) with similar EP waveshapes. In factor analysis each AER waveform is considered to be a combination of factors, basis waveshapes produced by separate signal generators.

The concept of factor analysis may be described in the following formula:

Wi is a set of AER waveshapes (evoked potentials) which are (i) responses at different head areas (different electrodes) to the same stimulus, or (ii) responses to different stimuli at the same scalp electrode.

$a_{11}$ is the contribution (factor score) of the factor $F_1$ (first basis waveshape) and $a_{12}$ is the factor score of the factor $F_2$, etc. Then:

$$W_1 = a_{11} F_1 + a_{12} F_2 + a_{13} F_3 \ldots a_{1k} F_k \quad \text{(Eq. 1)}$$

$$W_2 = a_{21} F_1 + a_{22} F_2 + a_{23} F_3 \ldots a_{2k} F_k$$

$$\vdots$$

$$W_N = a_N F_1 + a_{N2} F_2 + a_{N3} F_3 \ldots a_{Nk} F_k$$

K here is the number of factors that will describe a satisfactory amount of the energy in a set of N AER waveforms. Generally K is 7 or less and is considerably less than N, the number of AER waveforms in the set.

The "varimax procedure" is one method of selecting the shape of the basis or factor waveshapes, see John text, page 60. Principle component analysis attempts to define axes which can account for the energy in a set of signals in the most parsimonious way. These axes are the dimensions of the "signal space". A set of factors (i.e., axes) "spans" the space. The "varimax" rotation is a particular orientation of axes which yields dimensions corresponding well to physiological processes, see Kaiser et al, "A Method In Automatic Pattern Recognition In EEG" in Kellaway & Peterson, *Automation of Clinical Electroencoephalography* (Raven Press. NY 1973), pages 235-242, incorporated by reference herein.

Figure 2:
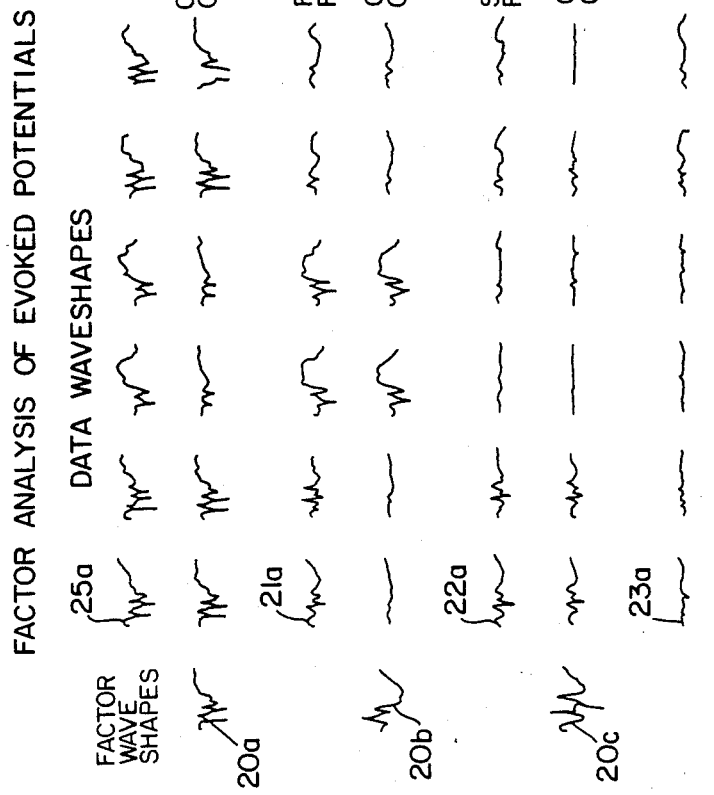
FIG. 2 is a diagram of typical factor waveshapes and data waveshapes.

As shown in FIG. 2, one may envision a first signal generator which produces a complicated basis waveshape 20a, and similarly second and third signal generators which produce complicated respective basis waveshapes 20b and 20c.

The signal generators may be adjusted, or programmed, to produce a desired arbitrary waveshape. The shape of the basis waveshapes 20a-20c are selected by using (i) experience based upon a long series of trials, or (ii) a varimax procedure, explained above. The basis waveshapes 20a-20c need not correspond to any known underlying brain wave shapes and in that sense might be considered as arbitrary waveshapes used for the purpose of the factor analysis.

The amount of the first basis waveshape 20a present in the AER waveshape 25a to be reconstructed is determined automatically by the computer 40, on the basis of its correlation to the brain waveshape 25a. The correlation is the contribution of that first basis waveshape 20a to the tested AER waveshape 25a.

The contribution of the first factor waveshape (first basis waveshape) 20a is subtracted from the AER 25a leaving a first residual 21a. For example, if the first basis waveshape 20a closely matches (i.e., is highly correlated with, the AER waveshape 25a, it may account for 80% of the energy of the AER waveshape 25a; in which case the first residual 21a would contain 20% of the energy of the AER waveshape 25a. The "weighing coefficient" or "loading factor" is the relative contribution of each factor. In the example the weighing coefficient of the first factor 20a is 0.8 (equal to 80%).

The contribution of the second factor 20b (second basis waveshape) is then ascertained and subtracted from the first residual 21a, which leaves the second residual 22a as its remainder.

The contribution of the third factor 20c (third basis waveshape) is then ascertained and subtracted from the second residual 22a, which leaves the third residual 23a as its remainder.

Generally, six to seven factors are sufficient to account for almost all the energy of the full set of 19 AER waveshapes recorded from all positions of the 10/20 System, leaving insignificant residuals.

In order to obtain a standardized set of factor descriptors of the morphology of AER waveshapes, it is necessary to carry out principal component analysis followed by Varimax rotation on the full set of 19 AER waveshapes, $W_i(t)$, recorded from each of a large number of normal subjects. This analysis yields a set of "General Factor Waveshapes", $F_j(t)$, capable of reconstructing the individual waveshapes $W_i(t)$ recorded from any electrode position i in any normal subject. Thus, $$W_i(t) = \sum_{j=1}^{k} a_{ij} F_j(t) \quad \text{(Eq. 2)}$$

For each electrode position i, the mean value $\bar{a}_{ij}$ and standard deviation $\sigma_{ij}$ are calculated from the distribution of the factor score $a_{ij}$, which describes the contributions of factor j to Wi in the normal population. It is now possible to describe any set of waveshapes $W_i(t)$ recorded from any individual in a way which will utilize these normative data to quantify abnormal AER morphology, by computing the Z-transform of the factor score, $a_{ij}$, to obtain the factor Z-score, $Z_{ij}$.

Thus, $$Z_{ij} = \frac{a_{ij} - \bar{a}_{ij}}{\delta_{ij}} \quad \text{(Eq. 3)}$$

wherein
  $a_{ij}$=factor score defining the contribution of factor j to waveshape recorded from electrode position i in patient
  $\bar{a}_{ij}$=mean value of $a_{ij}$ in normal population
  $\sigma_{ij}$=standard deviation of distribution of $a_{ij}$ in normal population $Z_{ij}$=factor Z-score rescaling the deviation of $a_{ij}$ from $a_{ij}$ into units of $\sigma_{ij}$ which reflect the *probability* of abnormality.

The effect of the Z-transform is to provide the common metric of "relative probability" in the dimensions (units) in which all features are stated. Relative probability means the probability of obtaining the observed value by chance in a member of the control group. In other words, the Z computation characterizes the individual's index value as a number of error steps from the control value and indicates the relative probability that this value did not occur by chance. This Z value, taken at each electrode, can be plotted in a topographical head-like display.

Using factor Z-scores to replace the original factor scores, Equation 2 can be rewritten as:

$$W_i(t) = \sum_{j=1}^{K} Z_{ij} F_j(t) \qquad \text{(Eq. 4)}$$

Once the factor waveshapes $F_j(t)$, and the values of $a_{ij}$ and $\sigma_{ij}$ have been ascertained for any defined stimulus condition, the probability that the set of AER waveshapes recorded from any patient under that stimulus condition displays abnormal morphology can be assessed objectively, as follows:

After recording the full set of AER's from the patient, they are reconstructed as well as possible as linear combinations of the general Factors, $F_j(t)$, with the contribution of each factor j to every waveshape i defined by the corresponding factor score, $a_{ij}$. The factor scores $a_{ij}$ are then subjected to Z-transform, such Z transformation being by the computer system 40 and under program control. This procedure decomposes the patient's AER waveshapes to a standardized description which permits the morphology to be compared quantitatively to the range of morphologies which can be encountered in the normal population. It should be emphasized that for cortical evoked potentials, there are a wide variety of normal waveshapes. Once the least square best fit reconstruction of the patient's AER's has been achieved, the "reconstruction error" of each waveshape $W_i(t)$ is computed. This difference between the actual AER and the factorial reconstruction quantifies the amount of energy in the patient's response which may lie outside the "normal signal space", and will be referred to as the residual, which is also Z-transformed.

The set of AER's recorded in any patient can now be represented by a set of color-coded topographic maps. The contribution of each factor and the amount of the residual are each represented by a separate map. The colors are used to encode the value of $Z_{ij}$ at each electrode position. Thus, these factor Z-score maps display the probability that each brain region shows an abnormal feature in its AER morphology.

The following is an example of the factor structure of the "evoked potential space". Average evoked potentials (AEP) were obtained from 54 normal adults in response to 100 blank flashes and to 100 random clicks. 19 electrodes were located on each of these subjects in accordance with the International 10/20 system. Principal component factor analysis, followed by Varimax rotation, as explained above, was used to ascertain the structure of the set of 19 visual evoked potentials (VEP's) and auditory evoked potentials (AEP's) obtained from each of the adult subjects. Five factors accounted for 70% of the variance of the visual evoked potential (VEP) set and 3 factors accounted for 62% of the variance of the auditory evoked potential (AEP) set. Each average was based upon 100 stimulus repetitions, so that the remaining variance was considered to be "noise".

The factor structure and the actual factor waveshapes were essentially identical in two split-half normal samples. The "norms" were obtained by computing means and standard deviations for the factor scores ($A_{ij}$) for each factor ($F_j$) required to reconstruct the evoked potential (i) recorded from each electrode (i) such that:

$$EP(i) = \sum_{j=1}^{K} A_{ij} F_j$$

Using these norms, factor scores, in every deviation (every electrode) from each subject were Z-transformed to estimate the probability that the observed response was abnormal. Interpolated topographic maps were constructed for each factor score. The maps were color coded to reflect the local probability of abnormality.

This method was used to evaluate VEP's and AEP's in a group of 18 normal subjects and in 8 pathological groups containing 158 patients with different disorders. Abnormal findings significant at the $P<0.05$ level are shown in Table I.

TABLE 1

| Group | n | \% Abnormal* Factor Scores in Variance Groups (VEP Only) - in Percentages | | | | | | Total Abnormal \% |
|---|---|---|---|---|---|---|---|---|
| | | FACTOR number in group | | | | | Residuals | |
| | | 1 | 2 | 3 | 4 | 5 | | |
| Normal 1 | 30 | 0 | 0 | 0 | 0 | 0 | 7 | 7 |
| Normal 2 | 24 | 0 | 4 | 0 | 0 | 0 | 0 | 4 |
| Normal 3 | 18 | 0 | 0 | 0 | 0 | 0 | 0 | 0 |
| Elderly Depressed | 18 | 17 | 17 | 11 | 11 | 22 | 28 | 50 |
| Unipolar Depressed | 23 | 17 | 35 | 22 | 22 | 22 | 70 | 70 |
| Bipolar Depressed | 24 | 17 | 21 | 38 | 13 | 17 | 71 | 75 |
| Schizophrenic | 21 | 0 | 10 | 0 | 0 | 0 | 0 | 10 |
| Alcoholics | 26 | 12 | 8 | 12 | 0 | 12 | 15 | 27 |
| Alzheimer | 12 | 8 | 17 | 0 | 8 | 0 | 17 | 25 |
| Vascular | 15 | 13 | 21 | 13 | 6 | 13 | 27 | 27 |
| Mild Head Injury | 19 | 5 | 5 | 5 | 0 | 0 | 11 | 26 |

*$[Z]<4.0$ on at lest 3 derivations for the same factor.

This method was also used to study the changes in organization of the "evoked potential space" during mental activity. VEP's were obtained from subjects during rest and during repeated periods of performance of a task requiring mental categorization of verbally presented pairs of words. Consistent effects of mental activity most marked in visual factors were found in groups of normal, depressed and schizophrenic subjects.

A preferred display is shown in FIG. 3. It is a topographic map which is color-coded and preferably shown on a high-quality color CRT (cathode ray tube) picture tube. The face plate 60 of the picture tube is shown with a head-like display 61 having nineteen areas 62 corresponding in location to the placement of the nineteen scalp electrodes in the International 10/20 System. Consequently, there are 19 boxes arranged in 5 rows with 2, 5, 5, 2 boxes in the rows. Each box corresponds to an electrode location on the head to form a topographic map.

The content of each box is shown in FIG. 4. There are two rows each composed of 5 vertical bars. The top row contains 5 bars depicting the factor $\underline{Z}$-scores corresponding to factors 1 to 5. The bottom row contains 5 bars which respectively depict: factor $\underline{Z}$-score for factor 6, factor $\underline{Z}$-score for factor 7, overall $$\text{deviation} = \left| \sum_{j=1}^{Z} z_{ij}^2 \right|^{1/2},$$

$\underline{Z}$-transformed residual error, $\underline{Z}$-transformed rms power of AER waveshape. Each of these 10 bars is color-coded to reflect the statistical probability that the AER morphology lies within normal limits.

The color coding is on a "flame scale" ("heat scale") in which light blue is a highly abnormal deficiency ($P<0.01$), less than reference norm), blue is a slightly abnormal deficiency ($P<0.05$ less than reference norm), gray is normal, red is a slightly abnormal excess ($P<0.01$ more than reference norm) of the contribution of any factor to the reconstruction of the AER waveshape in the corresponding brain region.

What is claimed is:

1. The method of analyzing the brain waves of a human subject to determine the presence, degree and type of evoked potential abnormality, the method consisting of the steps, in sequence, of:
    removably securing a plurality of electrodes $\underline{i}$ to the scalp of the patient, automatically presenting a sequence of stimuli to the patient to evoke brainwave potentials (EP) at the electrodes;
    detecting the said EP brainwaves, amplifying the detected brainwaves, converting the amplified brainwaves into digital form, averaging the digitized brainwaves to produce average evoked responses (AER) for analysis in a digital processing computer system having computer memory;
    decomposing the average evoked responses (AER) by factor analysis, in which each AER from each electrode is compared to pre-formulated factor waveforms stored in the computer memory to determine the amount of voltage that each pre-formulated factor waveform contributes to said AER to thereby produce a factor score $a_{ij}$, quantifying the contribution of each factor j to the AER from any electrode i;
    subjecting the results of the said factor score to $\underline{Z}$-transform, wherein each of said factor scores is compared to norms stored in the computer memory to produce a factor $\underline{Z}$-score, corresponding to a determination of waveshape normalcy and the degree of abnormality of each of said AER's and
    displaying the said normalcy and degree of abnormality on a color-coded topographic map comprising a head diagram in which each area of the head represents an electrode location and the colors represent normalcy and the degree of abnormality reflected by the factor $\underline{Z}$-score.

2. The method of claim 1 wherein the stimuli presented are a series of flashes or other visual stimuli to produce visual evoked potentials (VEP's).

3. The method of claim 1 wherein the stimuli presented are a series of clicks or other auditory stimuli to produce auditory evoked potentials (AEP's).

4. The method of claim 1 wherein the stimuli presented are a series of electrical shocks or other somatosensory stimuli to produce somatosensory evoked potentials (SEP's).

5. The method of claim 1 wherein the topographic map is an interpolated map.

6. The method of claim 1 wherein the topographic map is of each factor Z score.

7. The method of claim 1 in which the topographic map is a composite map of a plurality of factor Z scores.

8. A system for analyzing the brainwaves of a human subject to determine the presence, degree and type of evoked potential abnormality, the system consisting of:
    a plurality of electrodes, means for removably securing the plurality of electrodes to the scalp of the patient, stimuli means for automatically presenting a sequence of stimuli to the patient to evoke brainwave potentials (EP) at the electrodes;
    amplifier means for amplifying the evoked brainwaves, A/D converter means for converting the amplified brainwaves into digital brainwave form, averaging means for averaging the digitized brainwaves to provide average evoked responses (AER) for analysis in a digital processing computer system;
    computer means having a computer memory and calculation means for analyzing the average evoked responses by factor analysis, said computer means comparing each AER from each electrode to pre-formulated factor waveforms stored in the computer memory to determine the voltage that each pre-formulated factor waveform contributes to each AER said comparison producing a factor score $a_{ij}$ quantifying the contribution of each factor to the AER from any electrode;
    $\underline{Z}$-transform computer means for subjecting the said factor score to $\underline{Z}$-transform, statistical computing means for automatically comparing each of said factor scores to norms stored in the computer memory to produce a factor $\underline{Z}$ score providing a determination of normalcy versus the degree of abnormality; and
    display means to display the said normalcy and degree of abnormality on a color coded topographic map comprising a head diagram in which each area of the head represents an electrode location and the color represents normalcy and the degree of abnormality reflected by the factor $\underline{Z}$ score.

9. The system of claim 8 wherein the stimuli presented are a series of flashes or other visual stimuli to produce visual evoked potentials (VEP's).

10. The system of claim 8 wherein the stimuli presented are a series of clicks or other auditory stimuli to produce auditory evoked potentials (AEP's).

11. The system of claim 8 wherein the stimuli presented are a series of electrical shocks or other somatosensory stimuli to produce somatosensory evoked potentials (SEP's).

12. The system of claim 8 wherein the topographic map is an interpolated map.

13. The system of claim 8 wherein the topographic map is of each factor $\underline{Z}$ score.

14. The system of claim 8 in which the topographic map is a composite map of a plurality of factor $\underline{Z}$ scores.

* * * * *